United States Patent [19]

Devlin et al.

[11] Patent Number: 5,122,513

[45] Date of Patent: Jun. 16, 1992

[54] FISH GROWTH USING BOVINE PLACENTAL LACTOGEN

[75] Inventors: Robert H. Devlin, North Vancouver; Edward M. Donaldson, West Vancouver, both of Canada; Ernest G. Jaworski, St. Louis; Gwenn G. Krivi, Olivette, both of Mo.

[73] Assignee: Monsanto Company, St. Louis, Mo.

[21] Appl. No.: 671,233

[22] Filed: Mar. 19, 1991

[51] Int. Cl.⁵ .............................. A61K 37/36
[52] U.S. Cl. ........................ 514/12; 514/21; 530/399; 435/243; 435/252.3
[58] Field of Search ............ 514/144; 530/399; 435/243, 252.3

[56] References Cited

U.S. PATENT DOCUMENTS 4,689,402 8/1987 Sekine et al. ..................... 530/399
4,767,711 8/1988 Schuler et al. .................... 435/243

FOREIGN PATENT DOCUMENTS 0306470 3/1989 European Pat. Off. .

OTHER PUBLICATIONS

Chem. Abstracts, vol. 54, 1960, 18804g-i, Kosto et al.
Endocrinology, vol. 93, pp. 960-964 (1973), Clarke et al.
Endocrinology, vol. 113, pp. 2186-2194 (1983), Arima et al.
Endocrinology, vol. 111, pp. 2117-2124 (1982), Murthy et al.
Endocrinology, vol. 119, pp. 1343-1350 (1986), Byatt et al.
D. C. Cohen et al. *Gen. and Comparative Tech.* vol. 18:384-390 (1972).
D. A. Higgs et al. *Can. J. Zool.*, vol. 55, No. 6, 1048-1956 (1977).
J. A. Gill et al. *Bio/Technology*, vol. 3, 643-646 (1985).
Kiyoshi Asahina et al. *Gen and Comparative Endocrinology*, vol. 52, 426-437 (1983).
N. E. (Ted) Down et al. *Aquaculture*, 141-155 (1988).
N. E. (Ted) Down et al. *J. World Aquaculture Soc.*, vol. 20, No. 4, 181-187 (1989).
Patricia M. Schulte et. al. *Aquaculture*, vol. 76, 145-156 (1989).

*Primary Examiner*—Howard E. Schain
*Attorney, Agent, or Firm*—Dennis A. Bennett; Paul L. Passley; James C. Bolding

[57] ABSTRACT

A method is described for increasing growth of fish which comprises administering bovine placental lactogen.

6 Claims, No Drawings

FISH GROWTH USING BOVINE PLACENTAL LACTOGEN

This application relates to methods for enhancing growth of fish, more particularly, to methods involving the use of growth promoters.

BACKGROUND OF THE INVENTION

From the beginnings of recorded history, oceans, streams and lakes have been important sources of food, from which the aquatic animals occupying these bodies of water are gathered. Because of increasing populations, pollution, and over-harvesting in certain areas, these natural resources no longer can meet the growing demand placed on these food sources. Although conservation, enhancements, improved breeding and fish-farming have supplied part of the increased needs, these approaches will be insufficient to meet future world demands for animal protein. Biotechnological advances are having major beneficial effects on our society today, and application of such methods to aquaculture have begun. One approach has been to stimulate the growth of fish by use of growth hormones. For example, human growth hormone and ovine prolactin have been shown to enhance the growth of lower vertebrates (*Endocrinology* 1973, Vol. 93, No. 4., 960-964). The use of bovine somatotropin to increase the growth of salmon has been extensively described Can. J. Zoo. V. 55, No. 6, 1048-1056, 1977; *Bio/Technology* V. 3, 643-646, 1985; U.S. Pat. No. 4,689,402. However, not all growth hormones have proven effective. Two studies have found that human placental lactogen had no growth stimulating activity in lower vertebrates (Cohen et al., General and Comparative Endocrinology, 1972, Vol. 18: 384-390; Clarke et al. 1973, Endocrinology, Vol. 93, No. 4, 960-964. Clearly, improved methods for fish production are still desirable.

SUMMARY OF THE INVENTION

A method has now been discovered for increasing the growth of fish which comprises administration of bovine placental lactogen to the fish, in an amount effective to enhance growth. The method of the present invention is applicable to all fish. Fish, as used herein, means cold-blooded aquatic vertebrates commonly used for food. Particularly important fish are those normally raised by use of aquacultural methods in fish farms. Examples of such fish are salmon (e.g. Atlantic, Chinook and Coho salmon), trout, tilapia, striped bass, catfish and carp.

The method of the invention is applicable to fish of any age. Six months old fry exhibit an excellent growth response when treated with bovine placental lactogen. Preferably, treatment is commenced at an early age, and continued through the growth phase as required.

The treatment frequency can vary from daily treatments to single treatments every few weeks. The schedule of treatment depends upon the dosage of bovine placental lactogen administered, the size and maturity of the fish to be treated, the type of delivery system used, environmental conditions such as water temperature and length of daylight, as well as feeding schedules and type and amount of feed provided. For salmonids, water temperatures of about 10° C. to 15° C. are satisfactory. Daily feeding to satiation is recommended. One advantage of the method of the invention is improved feed conversion efficiencies. Typically, the fry are given single weekly treatments for up to 20 weeks or more. However, significant growth is observed with administration of single doses of bovine placental lactogen once a week for periods of one to eight weeks.

The bovine placental lactogen may be administered by injection intramuscularly or intraperitoneally. The bovine placental lactogen may be administered dissolved in saline, dispersed in oil, by pellet or by osmotic pump. Alternatively, the bovine placental lactogen may be administered by absorption through the gills of the fish. This is accomplished by first shocking the fish to dilate the gills by dipping into a saline solution; followed by dipping into water containing dissolved bovine placental lactogen. The duration of treatment depends on the concentration of bovine placental lactogen, the size of the fish and the desired dose to be delivered.

The amount of bovine placental lactogen effective to achieve a growth response in the fish varies with the species and age of the fish, environmental conditions, and amount of feed available. Typically, the dose ranges, but is not limited to, from 0.01 $\mu$g to 10 $\mu$g bovine placental lactogen per gram of fish, preferably, 0.5 $\mu$g to 5 $\mu$g per gram of fish.

Either naturally occurring bovine placental lactogen recovered from bovine placentas or recombinant bovine placental lactogen may be used in the practice of the invention. The production of naturally occurring bovine placental lactogen is described in Arima et al., *Endocrinology* 113, 2186-2194 (1983) and Byatt et al., *Endocrinology* 119, 1343-1350 (1986). Recombinant bovine placental lactogen is described in South Africa Patent 6,522 issued Jun. 28, 1989. A mutant form of bovine placental lactogen containing one or more amino acid substitutions may be used in the practice of the invention providing that the substitutions do not adversely affect the growth promoting properties exhibited by native bovine placental lactogen. Thus, variant forms of bovine placental lactogen would be expected to be suitable for the practice of the invention.

DESCRIPTION OF PREFERRED EMBODIMENTS

About 30 juvenile Coho (Oncorhynchus kisutch) salmon weighing between 7.0 and 7.9 grams are placed in each of seven tanks supplied with fresh water at a temperature of 15° C. and acclimated for one week. The fish in two tanks are given intraperitoneal injections each week of 5.0 $\mu$g of bovine serum albumin (BSA) per gram of fish. The fish in four tanks are given intraperitoneal injections of bovine placental lactogen (bPL). In two tanks, the dose is 0.5 $\mu$g/g and in the other two tanks, the dose is 5.0 $\mu$g/g. Each week, each fish is anaesthetized, injected, measured and weighed, and the dosage adjusted to the current weight of the specimens to maintain the indicated dosage. One tank held untreated fish which were measured at the beginning and end of the experiment. All proteins were dissolved in 0.9% saline before injection.

Throughout the experiment, feed is supplied to each tank to satiation (all they can eat at one feeding period without providing excess) twice daily and the total feed consumption is monitored. Feed conversion efficiencies are calculated by dividing the total gain in wet weight by the total consumption of dry feed. The data at the end of five weeks are shown in Table 1.

TABLE 1

| Treatment | Dosage | Fish Number | Weight (g) | length (mm) |
| --- | --- | --- | --- | --- |
| untreated | none | 24 | 11.6 | 96.9 |
| BSA | 5.0 μg/g | 29 | 10.3 | 93.7 |
|  |  | 30 | 11.0 | 96.0 |
| bPL | 0.5 μg/g | 29 | 15.7 | 106.3 |
|  |  | 30 | 15.8 | 106.3 |
| bPL | 5.0 μg/g | 29 | 21.5 | 116.2 |
|  |  | 30 | 22.7 | 119.0 |

The data show that BSA suppresses growth slightly, whereas, the bPL treated fish exhibit substantial growth measured either by weight or length gain. The 0.5 μg/g bPL treated fish show 35% weight gain and 10% length increase compared to the untreated control group. The 5.0 μg/g bPL treated fish show 91% weight gain and 21% length increase compared to the untreated control. The bPL increases the feed conversion by about 10 to 20 percent which means that bPL not only makes the fish grow faster, but it does so with less feed required to attain a particular size. Examination of the fish show that the bovine placental lactogen treated salmon exhibit clear indications of earlier smoltification as compared to the untreated controls, for example, by the disappearance of the vertical parr markings.

Although the invention has been illustrated by typical examples, it is not limited thereto. Changes and modifications of the examples of the invention herein chosen for purposes of disclosure can be made which do not constitute departure from the spirit and scope of the invention.

We claim:

1. A method for increasing the growth of fish which comprises administering to the fish, in an amount effective to enhance growth, bovine placental lactogen.

2. The method of claim 1 in which the amount of placental lactogen injected is 0.01 μg to 10 μg per gram of body weight.

3. The method of claim 2 in which the placental lactogen is administered by intraperitoneal injection.

4. The method of claim 3 in which the fish is a salmon.

5. The method of claim 4 in which the placental lactogen is injected weekly for a period of about one to six weeks.

6. The method of claim 1 in which said fish begins to undergo smoltification within five weeks of initiation of said method.

* * * * *